US006626052B1

(12) United States Patent
Martin et al.

(10) Patent No.: US 6,626,052 B1
(45) Date of Patent: Sep. 30, 2003

(54) METHOD AND APPARATUS FOR ARTIFICIAL WEATHERING

(75) Inventors: Jonathan Martin, Gaithersburg, MD (US); Joannie Chin, Frederick, MD (US)

(73) Assignee: The United States of America as represented by the Secretary of the Commerce, Washington, DC (US)

( * ) Notice: Subject to any disclaimer, the term of this patent is extended or adjusted under 35 U.S.C. 154(b) by 0 days.

(21) Appl. No.: 09/180,079

(22) PCT Filed: Apr. 25, 1997

(86) PCT No.: PCT/US97/07004

§ 371 (c)(1),
(2), (4) Date: Aug. 2, 1999

(87) PCT Pub. No.: WO97/41417

PCT Pub. Date: Nov. 6, 1997

Related U.S. Application Data

(60) Provisional application No. 60/016,731, filed on May 2, 1996.

(51) Int. Cl.[7] .............................................. G01N 17/00
(52) U.S. Cl. ....................... 73/865.6; 356/236; 250/228
(58) Field of Search ...................... 73/865.6; 356/236; 250/228

(56) References Cited

U.S. PATENT DOCUMENTS

| | | | |
|---|---|---|---|
| 1,818,687 A | 8/1931 | Buttolph .................. 73/150 R |
| 3,426,590 A | 2/1969 | Suga ......................... 73/150 R |
| 3,664,188 A | 5/1972 | Kockott ..................... 73/150 R |
| 3,686,940 A | * 8/1972 | Kockott ..................... 73/150 R |
| 3,847,024 A | 11/1974 | Beever et al. ............. 73/865.6 |
| 3,874,799 A | * 4/1975 | Isaacs et al. ................ 356/402 |
| 4,012,954 A | 3/1977 | Klippert ................... 73/150 R |
| 4,232,971 A | 11/1980 | Suga .......................... 356/446 |
| 4,391,522 A | 7/1983 | Schmid et al. .............. 356/326 |
| 4,487,504 A | 12/1984 | Goldsmith .................. 356/323 |
| 4,540,281 A | 9/1985 | Akiyama .................... 356/325 |
| 4,618,776 A | 10/1986 | Sturm et al. ................ 250/372 |
| 4,644,166 A | 2/1987 | Sturm et al. ................ 250/372 |
| 4,747,645 A | 5/1988 | Rudzki ........................ 356/51 |
| 4,807,247 A | 2/1989 | Robbins, III ................. 374/57 |
| 4,817,447 A | 4/1989 | Kashima et al. ........... 73/865.6 |
| 4,900,923 A | * 2/1990 | Gerlinger .................... 250/228 |
| 5,136,886 A | * 8/1992 | Neigoff et al. ............. 73/865.6 |
| 5,138,892 A | 8/1992 | Suga ......................... 73/865.6 |
| 5,206,518 A | 4/1993 | Fedor et al. ............ 250/504 R |
| 5,220,840 A | 6/1993 | Neigoff et al. ............. 73/865.6 |
| 5,305,634 A | * 4/1994 | Suga et al. .................... 73/86 |
| 5,476,636 A | 12/1995 | Tomiita et al. ............... 422/53 |
| 5,479,009 A | 12/1995 | Jablonski et al. ........... 250/229 |
| 5,519,534 A | * 5/1996 | Smith et al. ................. 359/599 |
| 5,734,115 A | * 3/1998 | Camp et al. ............... 73/865.6 |

OTHER PUBLICATIONS

Optronik, GmbH, "Integrating Photometer ITS10" available from the Internet at http://www.optronik.de/its10en.pdf.*

* cited by examiner

Primary Examiner—Hezron Williams
Assistant Examiner—David Rogers
(74) Attorney, Agent, or Firm—Millen, White, Zelano & Branigan, P.C.

(57) ABSTRACT

A method and apparatus for irradiating a specimen with a beam of radiation are provided. The method comprises the steps of providing an integrating sphere, a radiation source radiatively communicating with the sphere, and a specimen, the integrating sphere radiatively communicating with the specimen through an aperture in the sphere. The apparatus comprises a radiation source, an integrating sphere in radiative communication with the radiation source, and a specimen holder in radiative communication with the integrating sphere. The disclosed apparatus and method allow the irradiance of a beam of radiation impinging on the specimen to be maintained at a uniform level across the width of the beam to allow quantitative specimen evaluation.

26 Claims, 9 Drawing Sheets

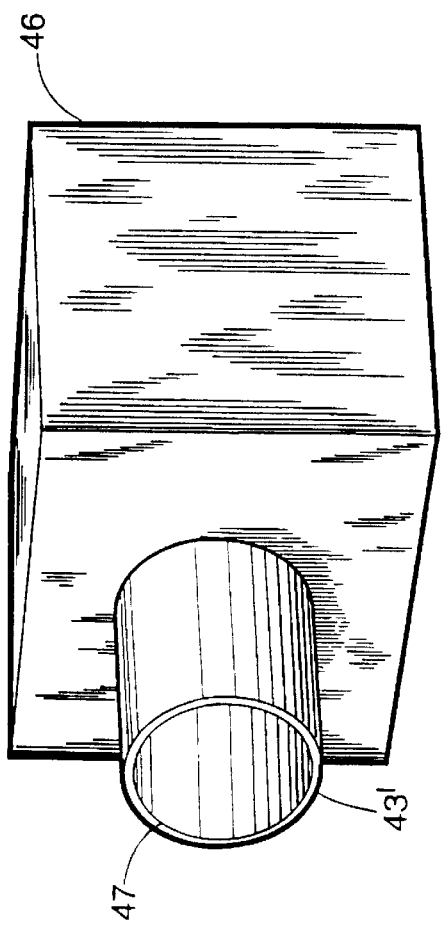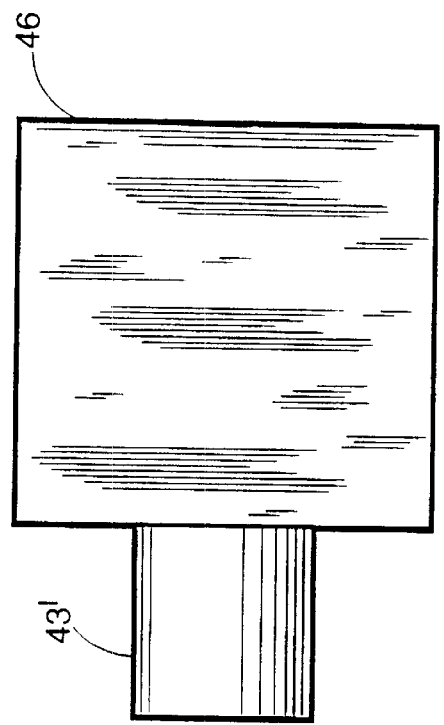

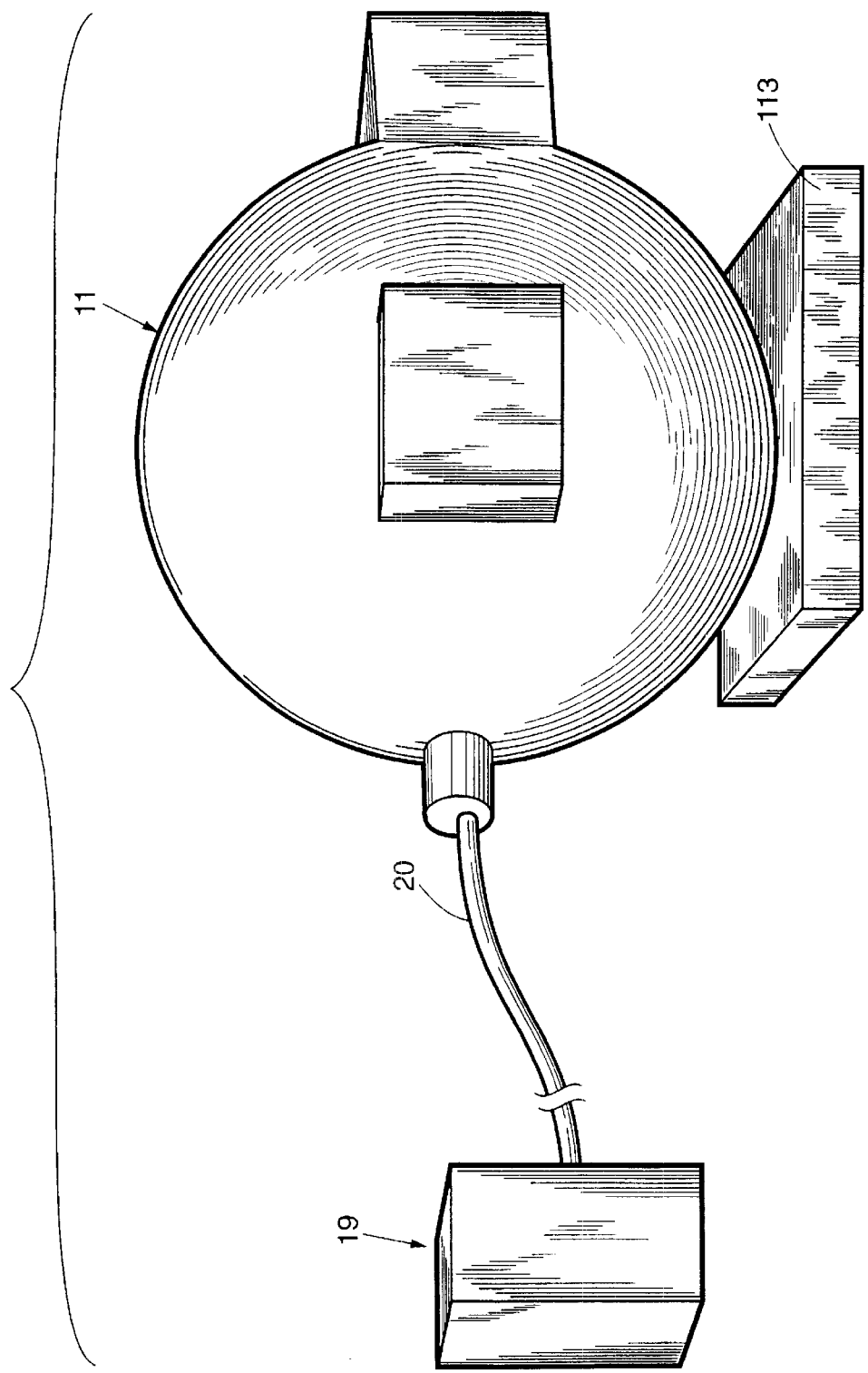

METHOD AND APPARATUS FOR ARTIFICIAL WEATHERING

This application claims the benefit of Provisional application No. 60/016,731, filed May 2, 1996.

TECHNICAL FIELD OF THE INVENTION

The present invention is directed toward a method and apparatus for applying radiation to a specimen. In one embodiment, the invention is directed toward a method and apparatus for artificially weathering a specimen by irradiating the specimen with ultraviolet light.

BACKGROUND OF THE INVENTION

Materials such as textiles, rubber, leather, plastics, construction materials, and so forth are affected by the influence of sunlight and other climatic factors, such as moisture, temperature, and humidity. The effects of sunlight, particularly the ultraviolet component of sunlight, may cause changes in the molecular structure of such materials, which changes may be observed macroscopically as changes in the mechanical, electrical, optical, or other properties of the materials. In general, the change in properties is not favorable, and sunlight is thus said to cause such materials to degrade.

The degrading effects of ultraviolet light can be difficult to quantify, especially inasmuch as a number of other environmental and material factors will affect the rate at which such materials degrade. For example, various materials exposed to the same environmental conditions will all degrade at different rates. Moreover, the rate at which any one material will degrade varies widely depending on the environment in which the material is placed. In particular, factors such as humidity, moisture, temperature, acid deposition species and exposure to corrosive chemicals, and mechanical loading can cause dramatic variations in the service life of any such material. The particular combination of factors that will affect a specimen of material and the effect of any one of these factors on the specimen will differ with the application to which the specimen is put, the environment into which the specimen is placed, and the time of exposure to the environment.

Prior to the commercial introduction of an outdoor material, the weathering properties of the material should be known so that a useful service life may be estimated. In practice, the service life may be empirically estimated by placing a specimen of the material in its intended environment and measuring the useful service life. Because an empirical determination may require several months or years, however, the prior art has provided exposure chambers wherein the effects of sunlight and other environmental conditions may be simulated and accelerated. In a typical prior art exposure chamber, a specimen is placed in a light communicating relationship with a source of ultraviolet light, and other environmental factors, such as moisture and temperature, are monitored and/or controlled. The amount of ultraviolet light impinging on the specimen also may be controlled, and this amount typically is selected to simulate accelerated exposure to sunlight.

The usefulness of such an artificial weathering apparatus depends on a number of factors, one of the most important of which is the ability to control the spectral irradiance of the radiation impinging upon the test specimen. Although such control is desirable, it is particularly difficult to attain. One difficulty is that the light output of ultraviolet light sources such as xenon lamps is highly nonuniform. At any given moment, the radiance from one portion of the light source may vary from the radiance from another portion of the light source, particularly when the light source is an elongate bulb. Thus, the irradiance of a radiation beam impinging on a test specimen may vary across the surface area of the test specimen. Moreover, the overall radiance, or intensity of light flux, produced by such light sources may decrease as the light source ages, thus making it difficult to provide a prolonged uniform testing environment for a test specimen.

Another difficulty in achieving uniformity of irradiation arises when it is desired to perform an experiment on plural test specimens. The light radiance from plural sources likely will vary from one light source to another. Thus, to ensure accuracy of experimentation, it is often desired to use the same light source to irradiate all of the samples. This can be difficult when the number of samples is great, and may necessitate seriatim testing of the specimens, thus lengthening the time required for the test. Moreover, because the radiance from even a single light source will vary over time, consistent sample irradiance can be difficult even when the tests are conducted using a single source of ultraviolet radiation.

The prior art has provided a number of attempts at solving the problem of nonuniformity in irradiance of test specimens. For example, U.S. Pat. No. 5,206,518 is said to disclose a weathering apparatus, including a ballast arrangement connected to the light source for controlling the amount of power the light source receives from a power source. A controller is said to be connected to the ballast arrangement, to produce a ballast control signal for controlling operation of the ballast arrangement according to a desired set-point value. U.S. Pat. No. 5,220,840 is said to disclose a method of calibrating the light output of a multi-lamp testing chamber, the method including steps of continuous adjustment of the power to each lamp. These proposed solutions are somewhat unsatisfactory, inasmuch as each is complex and cumbersome. Moreover, although in each case uniformity of irradiance is said to be achieved over one dimension, these references do not specifically address the problem of irradiance uniformity over a two-dimensional area of an irradiated specimen.

Another difficulty encountered in prior art artificial weathering apparatuses is that of quantitatively evaluating the effects of other environmental variables on the degradation of the specimen. If the uniformity of irradiance of impinging radiation on the specimen is not known, it will be difficult or impossible to determine the significance of environmental factors other than ultraviolet light. The prior art is not believed to have addressed this problem. For example, U.S. Pat. Nos. 3,664,188 and 4,012,954 each purport to disclose a testing apparatus in which certain environmental conditions may be varied. Neither reference, however, addresses the problem of irradiance uniformity.

It is a general object of the present invention to provide a method and apparatus for irradiating a specimen. Another general object of the invention is to provide a method and apparatus for irradiating a specimen wherein other environmental factors may be variably controlled.

SUMMARY OF THE INVENTION

The inventors have discovered that the foregoing general objects may be satisfied by the use of an integrating sphere to provide a uniform radiation source for uniform irradiation of test specimens. An integrating sphere may be defined as a hollow chamber, preferably spherical or generally spherical, that has an inner surface including a highly reflective radiation diffusing material, either in the form of a coating or a monolithic wall material. When radiation is introduced into the interior of the sphere, the radiation is reflected off of the inner surface in all directions. After many reflections and re-reflections, the radiation flux within the sphere will be spatially integrated in a uniform distribution in all dimensions. A beam of radiation exiting an aperture in the integrating sphere will have a uniform radiance over the width, and preferably over the area, of the beam. Moreover, if plural apertures are provided in the integrating sphere, the radiance of each beam exiting the sphere will be uniform from beam to beam. These principles of integrating spheres are known, and have been described in a number of references in the art, such as Sumpner, *The Proceedings of the Physical Society of London*, 12:10 (1892) and Edwards et al., *Journal of Applied Optics*, 51:1279 (1961). Heretofore, integrating spheres have been used as sources of uniform light for measurement of the optical properties of a test specimen, as illustrated, for example, in U.S. Pat. No. 3,847,024. As is typified by this reference, the measuring apparatus includes an integrating sphere and specimen disposed within the sphere. The apparatus further includes a light source directly irradiating the specimen. A photomultiplier alternatively measures light reflected from the specimen and light reflected from a portion of the sphere. The prior art has failed to appreciate that an integrating sphere may be employed as a radiation source in an artificial weathering apparatus or method, and has further failed to appreciate that plural specimens may be simultaneously irradiated with radiation from an integrating sphere.

In accordance with the invention, a method and apparatus are provided. In one embodiment, the method comprises the steps of providing an integrating sphere and a radiation source in radiative communication with the interior of the integrating sphere, the integrating sphere having an aperture, whereby a radiation beam having a width and a substantially uniform radiance over the width of the beam is communicated from the integrating sphere. The method further includes a step of placing a specimen in radiative communication with the aperture such that at least a portion of the radiation communicated from the integrating sphere impinges on the specimen. The apparatus of the preferred embodiment comprises an integrating sphere having at least one aperture, a radiation source in radiative communication with the interior of the integrating sphere, and a specimen holder disposed externally with respect to the integrating sphere, the integrating sphere radiatively communicating with the specimen holder through the aperture. In other embodiments of the invention, a specimen is placed within the integrating sphere and is irradiated with radiation therein.

Other features and objects of the invention will be apparent from the following description of the invention and appended claims.

DESCRIPTION OF THE DRAWINGS

FIG. 5 is a perspective view of one embodiment of a conduit and specimen holder assembly for an apparatus in accordance with the invention.

FIG. 6 is a side elevational view of the conduit and specimen holder assembly shown in FIG. 5.

FIG. 10 is a perspective view of an apparatus in accordance with another embodiment of the invention.

DESCRIPTION OF THE INVENTION

The invention makes use of integrating sphere technology, which technology is based on Lambert's cosine law:

$$J_\theta = I_0 \cos \theta.$$

This law specifies that the intensity of light reflected from an ideally reflective surface is proportional to the cosine of the angle at which the light impinges on the surface. A surface is said to be Lambertian, or an ideal diffuser of light, if the intensity of the radiation reflected from that surface varies with the cosine of the angle to the surface. When the interior wall surface of a chamber is substantially Lambertian or coated to render the surface Lambertian, light will be reflected and re-reflected off of the wall surface, whereby the radiation flux within the integrating sphere will become homogenized. The homogenization of the radiation flux may be accomplished without the need for lenses and other imaging optic components.

Figure 1:
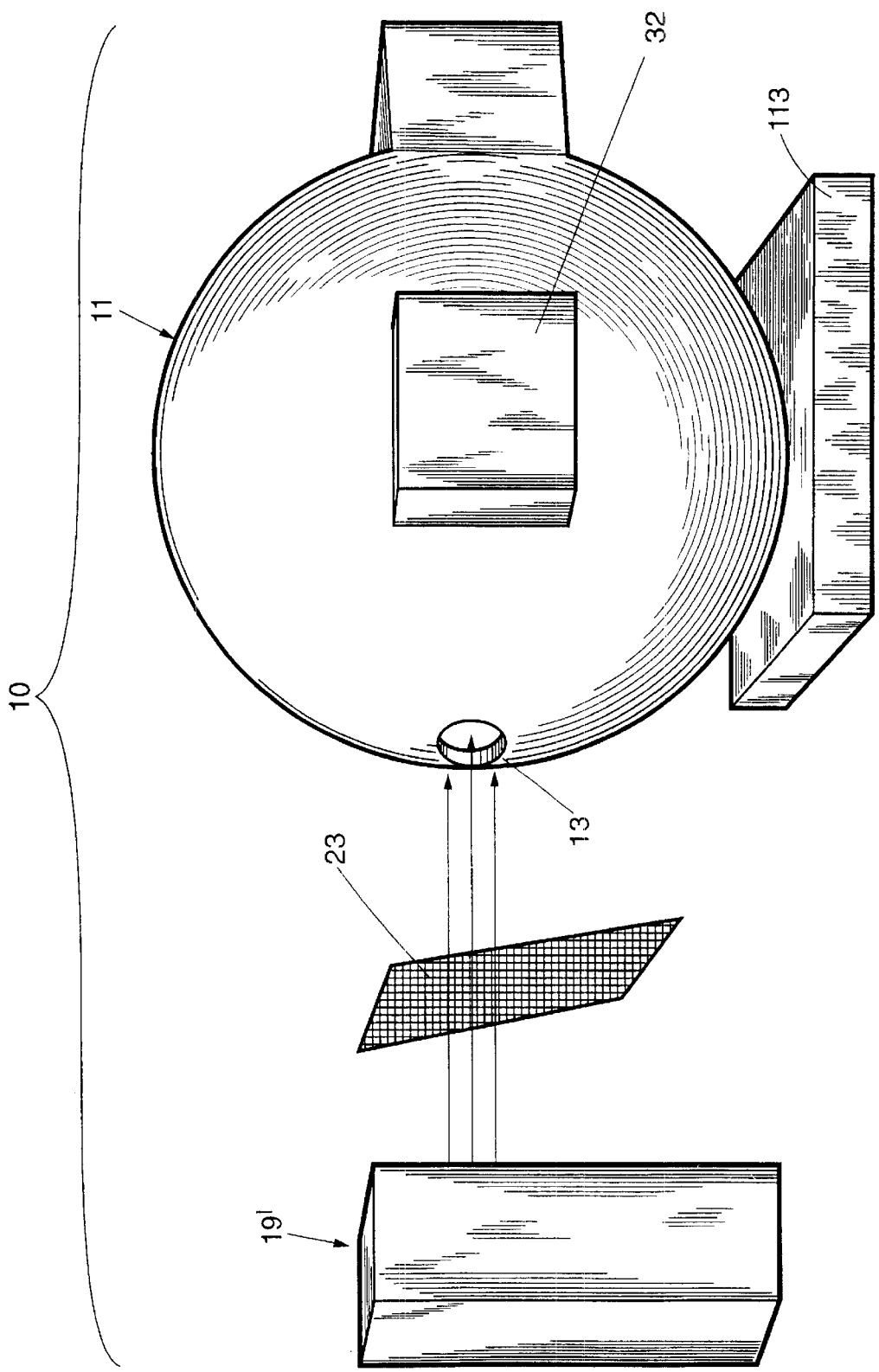
FIG. 1 is a perspective view of an apparatus in accordance with the present invention.
Figure 2:
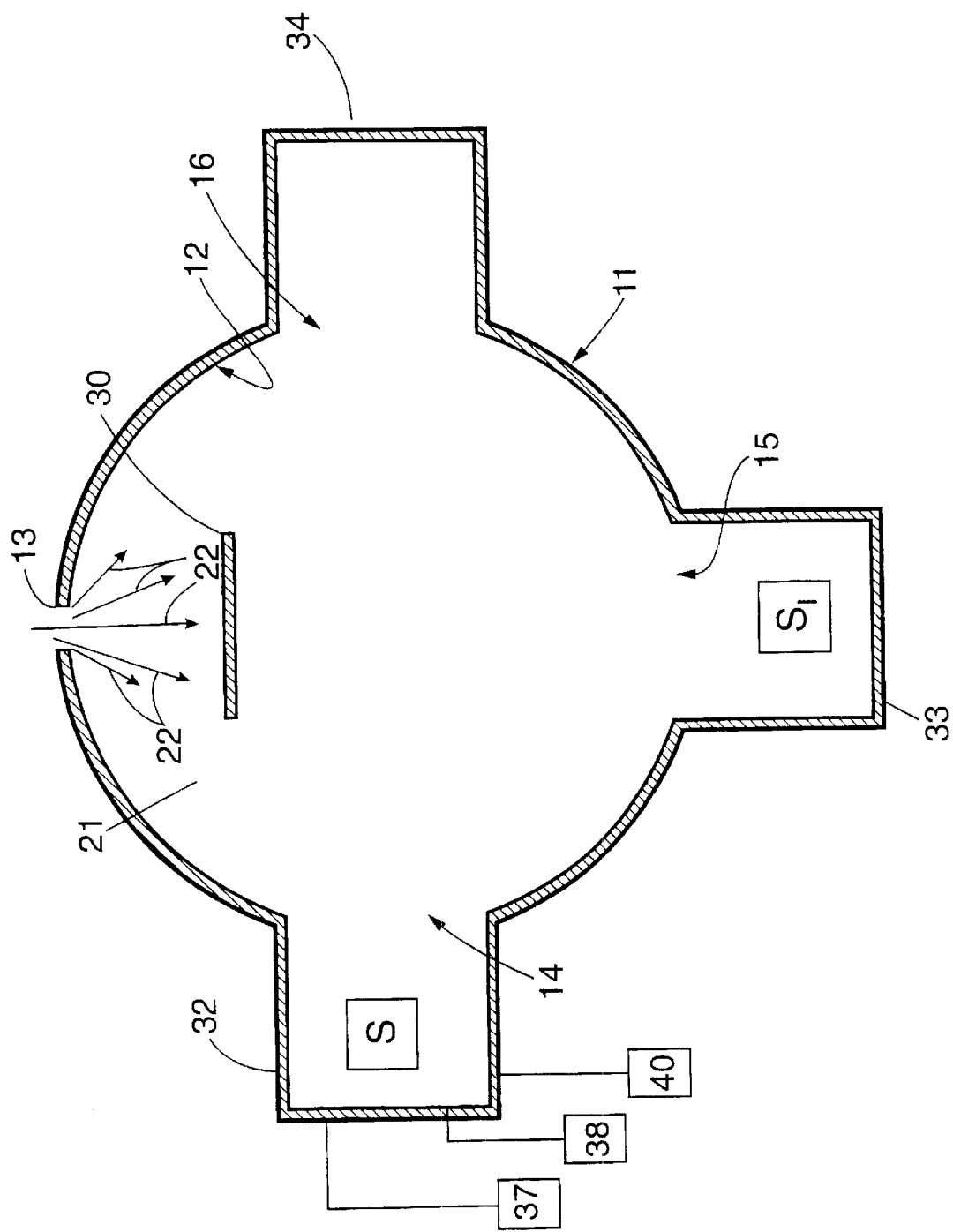
FIG. 2 is a cut-away plan view of the integrating sphere of the apparatus shown in FIG. 1.
Figure 3:
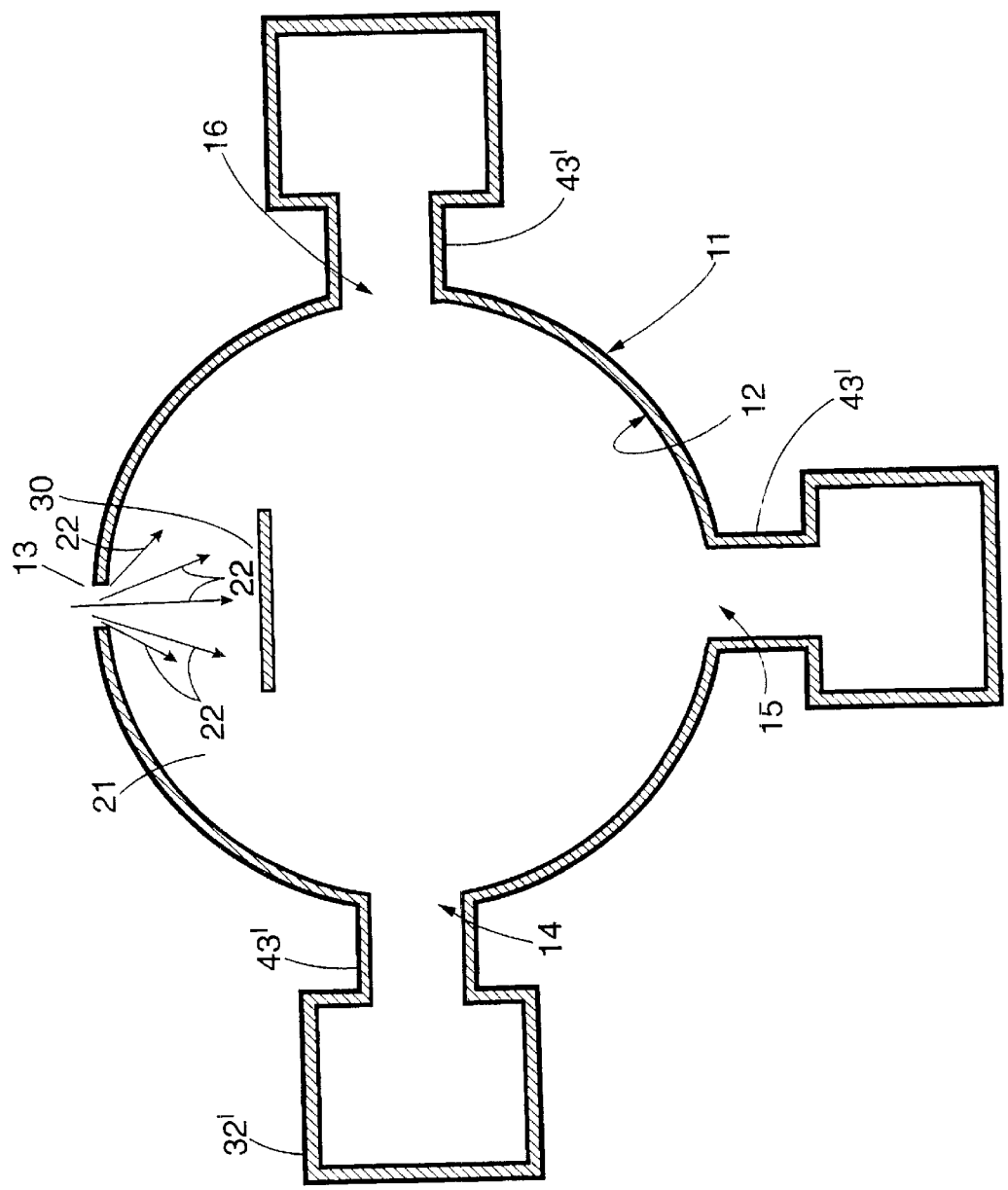
FIG. 3 is a cut-away plan view of an alternative embodiment of the integrating sphere of the apparatus of the invention.

As illustrated in FIGS. 1 through 3, the apparatus 10 of the invention includes an integrating sphere 11 having an interior cavity 21 and an inner surface or wall 12 (shown in FIGS. 2–3), the wall 12 having a highly reflecting Lambertian surface. The integrating sphere 11 is constructed of hemispherical halves resting on a base 113. The wall 12 of the sphere may itself comprise a Lambertian material, such as polytetrafluoroethylene, or the wall 12 may be coated with a reflective material such as barium sulfate to provide a Lambertian surface. As light is diffusely reflected and re-reflected within the integrating sphere 11, the radiant flux within the sphere will be homogenized, and will become highly uniform throughout the sphere 11.

The integrating sphere 11 has an inlet aperture 13. Preferably, the integrating sphere 11 also includes at least one exit aperture 14, and more preferably includes additional exit apertures 15, 16. A beam of light exiting the integrating sphere 11 through one of the exit apertures 14, 15, 16 will have a width and a substantially uniform radiance over the width of the beam. Preferably, the beam will have a cross-sectional area and a substantially uniform radiance over the cross sectional area of the beam. Moreover, the radiance of plural beams existing through exit apertures 14, 15, 16 will be uniform from beam to beam, as well as spatially uniform over the area of each beam. Additional apertures may be provided in the integrating sphere if desired, although the total aperture area including the inlet aperture 13 preferably should not exceed about 5% of the surface area of the wall 12.

The size of the integrating sphere preferably is chosen as is necessary for the operating conditions of the apparatus 10. Various sizes are possible, and the integrating sphere may have a diameter ranging from, for example, about 10 cm to about 2 m. Suitable integrating spheres are commercially available from a number of manufacturers, for example, from Labsphere (North Sutton, N.H.) under the name Unisource 4000. The exit apertures 14, 15, 16 and inlet aperture 13 may have any suitable dimensions. For example, when the integrating sphere has a diameter of about 50 cm, each exit aperture may be a circular opening having a diameter of about 12 cm, and the inlet aperture may have a diameter ranging from about 1 cm to about 10 cm. Each of the apertures may be provided with a removable cap (not shown) to block radiation from exiting the sphere through the aperture.

The integrating sphere is placed in radiative communication with a radiation source, which preferably is a source of ultraviolet light. The invention is not limited to a particular source of ultraviolet light, and sources such as xenon lamps, mercury arc lamps, carbon arc lamps, globars, halogen lamps, lasers, fluorescent bulbs, metal halide lamps, tungsten-halogen lamps, and the like may be employed. The wattage may range from a few watts to 1,000 watts, 25,000 watts or more. In accordance with a preferred embodiment of the invention, the radiation source is an ultraviolet lamp manufactured by Orc Lighting Products under Model No. XM12000 WC or a 1,000 watt ultraviolet lamp sold by ILC.

To provide radiative communication between the radiation source and the integrating sphere, the radiation source may be placed directly within the integrating sphere, or may be disposed in an exit aperature. In a preferred embodiment, however, the radiation source is disposed externally with respect to intergrating sphere, as illustrated in FIGS. 1 and 10. As illustrated in FIG. 10, the apparatus may include a conduit 20 for transmitting light from a radiation source 19 to the interior cavity of the integrating sphere 11. The conduit may be, for example, a fiber option connection. Alternatively, as shown in FIG. 1, radiation from source 19' may be directly introduced into the interior cavity 21.

Figure 9:
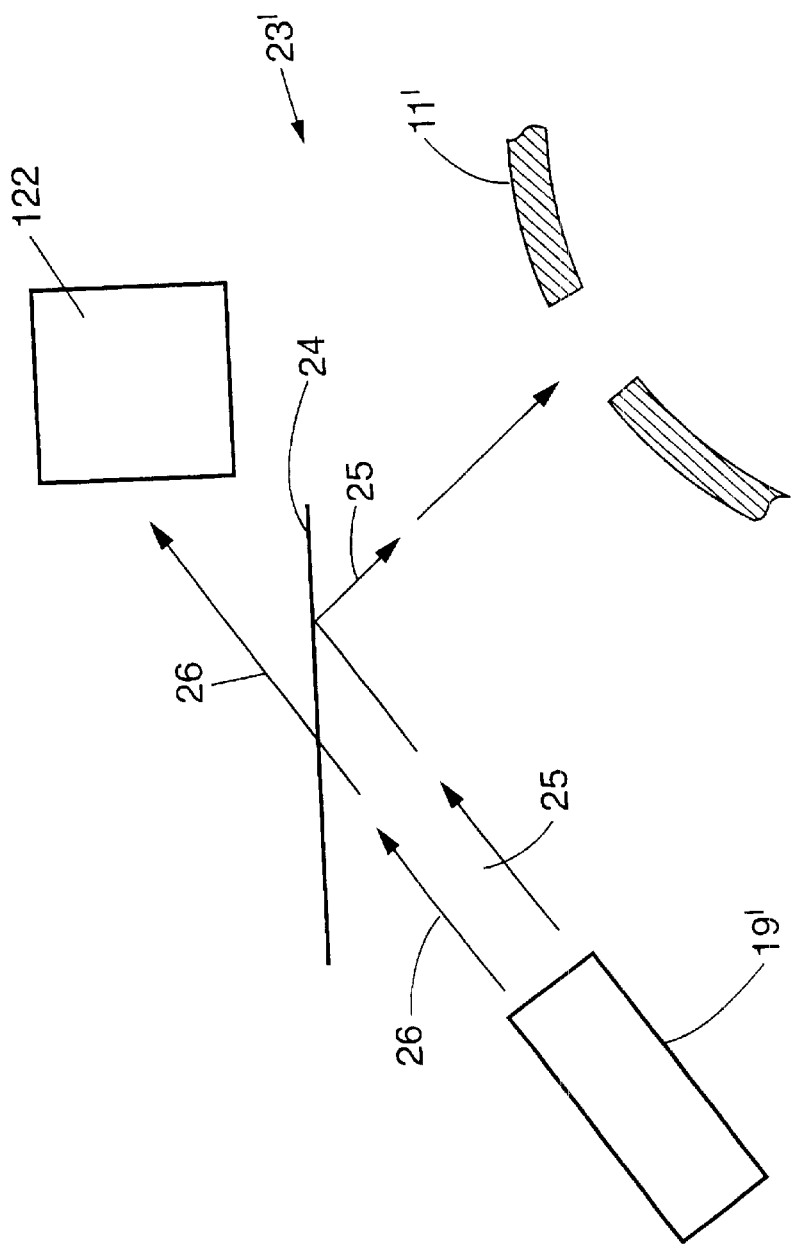
FIG. 9 is a schematic view of one embodiment of a filter in accordance with the invention.

Typical sources of ultraviolet light generate light having a number of wavelength components, including not only the desired ultraviolet light component, but also several other undesired wavelengths of radiation. For example, the light source may generate visible and infrared light on the one hand, and ultraviolet light having a wavelength of below 290 nm on the other hand. The infrared and visible wavelengths often are undesirable because they may cause the temperature within the integrating sphere to increase to an undesirably high level. Elevated temperatures within the integrating sphere may cause the sphere to become warped or otherwise damaged. Moreover, although it may be desired to test the effects on a specimen of radiation in a thermally elevated environment, infrared and visible wavelengths may cause the temperature within the sphere or of an irradiated specimen to rise to levels far beyond what would reasonably be expected during the service life of the specimen. Conversely, with respect to ultraviolet wavelengths below about 290 nm, such wavelengths are not naturally observed, and it is therefore desirable to filter out such wavelengths when simulating exposure to natural sunlight. Accordingly, in the preferred embodiment of the invention, a filter 23 desirably is interposed between the light source 19' and the integrating sphere 11. The filter 23 may comprise, for example, an ultraviolet cutoff filter sold under the name WG 295 by Melles Groit or an interference filter sold by Barr Associates. In the preferred embodiment of the invention, however, the filter 23' comprises a dichroic mirror 24, as shown in FIG. 9. Suitable dichroic mirrors are available from Oriel Corporation under the name Ultraviolet Long Pass Filters.

Radiation from a light source 19' includes a desired ultraviolet component as represented by arrow 25 and undesired higher wavelengths as represented by arrow 26. Ultraviolet wavelengths 25 are irradiated onto the mirror 24, and are reflected off of the dichroic mirror 24 and toward the integrating sphere 11'. The undesired wavelengths 26 pass through the mirror 24 and are directed toward a heat sink 122, which may comprise, for example, a solid block of copper. Other filters may be employed, for example, if it is desired to introduce electromagnetic radiation having wavelengths within a band of desired wavelengths into the integrating sphere.

With reference to FIGS. 2 and 3, radiation (represented by arrows 22) directed toward the interior cavity 21 of the integrating sphere 11 is reflected and re-reflected off of the Lambertian wall 12 until it exits the integrating sphere 11 through an exit aperture 14, 15, 16. The integrating sphere 11 preferably includes a baffle 30 to prevent incoming light from exiting directly through one of the exit apertures 15. The surface of the baffle 30 preferably is Lambertian or is coated such that the surface is rendered Lambertian. Plural baffles may be employed within the sphere if desired.

Radiation beams exiting the integrating sphere through one of the exit apertures 14, 15, 16 will have a width and a radiance that is substantially uniform over the width. In most or all cases, the radiance of the radiation beam will be uniform over a cross sectional area of the beam, and the radiance of plural beams of radiation exiting through similarly sized apertures will be uniform from beam to beam. When the radiation source is disposed externally with respect to the integrating sphere, as is preferred, it will be very easy to change the radiation source (such as by adding or removing ultraviolet bulbs) or to adjust the wavelengths of light that are permitted to enter the integrating sphere. If desired, a sensor (not shown) may be placed within the integrating sphere to monitor the radiation flux within the integrating sphere. When used, the sensor should be protected from direct irradiance from the light source, such as, for example, with a baffle interposed between the light source and sensor. If the radiation flux is observed to decrease or otherwise change over time, suitable compensation may be made in the radiation entering the integrating sphere. Extended irradiation of one or more specimens at constant irradiance over time thus may be achieved.

In accordance with the invention, a specimen is placed in radiative communication with the aperture of the integrating sphere such that radiation exiting the integrating sphere impinges on and irradiates the specimen. The specimen may be any tangible thing, and it is not intended to limit the invention to particular types of specimens that may be tested in conjunction with the invention. Ordinarily, a specimen will comprise a material that will normally be expected to be exposed to ultraviolet radiation. Such materials may include, for example, structural materials such as tensile fabrics, geotextiles, automobile tires, structural composite materials, asphalts, roofing materials, and so forth. Other nonstructural materials that may be tested in conjunction with the invention include materials such as coatings, nonstructural textiles, vinyl, plastics, paper, leather, nonstructural rubber and so forth.

Preferably, the specimen is irradiated for a time sufficient to cause a measurable change in a property of a specimen. Preferably, the specimen is irradiated with light having wavelengths ranging from about 290 nm to about 500 nm to thereby simulate the ultraviolet spectrum of natural sunlight and to thereby artificially weather the specimen. Many material properties are altered by electromagnetic radiation, particularly lower wavelength radiation such as ultraviolet radiation. The property that is affected may include, for example, any change observable on a molecular level. Such properties include any property that may be spectrographically measured, such as, for example, using IR spectroscopy, UV spectroscopy, NMR spectroscopy, or other methods. The property that is affected also may be any property that may be macroscopically observed, such as, for example, changes in color, appearance, strength, weight, conductivity, or any other physical property.

To irradiate a specimen, the specimen may be placed within the integrating sphere. Preferably, however, the specimen is disposed within a specimen holder that is itself disposed externally with respect to the integrating sphere. As shown in FIGS. 1–3, a specimen holder 32 or 32' may be attached to the integrating sphere 11 at the exit aperture 14. In accordance with the preferred embodiment of the invention, plural specimen holders 32, 33, 34, as shown in FIG. 2, are in radiative communication with the integrating sphere 11 to allow simultaneous irradiation of plural specimens. The specimen holder may be any container or retaining device to retain a specimen in radiative communication with the integrating sphere 11. Preferably, each of the specimen holders 32, 33, 34 comprises an enclosed or substantially enclosed chamber, such as an aluminum box, whereby the environmental conditions within the chamber may be controlled and monitored. Each of the specimen holders 32, 33, 34 preferably is removable from the apparatus so that substitution of new specimens disposed within new specimen holders may be easily accomplished. Inasmuch as the irradiance of radiation impinging on the specimen from a point source will decrease inversely as the square of the distance of the specimen from the radiation source, the specimen holders are preferably equidistant from the apertures.

In accordance with the most preferred embodiment, the apparatus has components for independently controlling at least one environmental condition within each of the specimen holders. For example, as shown in FIG. 2 with respect only to specimen holder 32, the apparatus may include means 37 associated with one or more of the specimen holders for controlling the temperature within the specimen holder 32. Such temperature control means may comprise, for example, heating and/or cooling coils, or may alternatively comprise a ventilation system for introducing hot or cold air into the specimen holder 32. The apparatus may further include means 38 for controlling the ambient humidity within the specimen holder 32. Such means 38 may include, for example, a source of moisture or a ventilation system for introducing air of a predetermined level of humidity into the specimen holder 32. In another embodiment of the invention, the apparatus may include means 40 for applying a static or cyclically varying mechanical load to a specimen disposed within the specimen holder 32. Such means may comprise, for example, tensioning grips, compression grips, bending devices, and the like. Those of ordinary skill in the art will appreciate that other components for controlling these and other environmental conditions within the specimen holders may be provided. In addition, the specimen holders may include sensors (not shown) for monitoring environmental conditions such as temperature and humidity therewithin to assist an operator in controlling the environmental conditions within the specimen holder.

If it is desired to place a specimen or specimens within the integrating sphere, the integrating sphere may itself be provided with similar components for controlling an environmental condition within the sphere or within a portion of the sphere that retains an irradiated specimen. For example, the interior of the integrating sphere may include one or more specimen holders, and one or more of the specimen holders may be provided with means for controlling an environmental condition therewithin.

The specimen holders may be attached directly to the integrating sphere at the apertures. In this embodiment, couplings (not shown) such as bolts or screws or other optical mounts may be used to removably fasten the specimen holders to the integrating sphere. In a preferred embodiment of the invention, however, the specimen holders are not attached directly to the integrating sphere, but instead are in radiative communication with the integrating sphere through a conduit, which itself preferably is attached directly to the integrating sphere. A conduit in accordance with the invention may be any instrumentality that permits radiation emitted from an aperture in the integrating sphere to be communicated to a specimen holder, preferably while allowing the radiance uniformity of a beam of such radiation to be maintained. The prior art is not known to teach or suggest the use of such a conduit. Use of a conduit increases the flexibility of the design of the apparatus, inasmuch as the conduit allows a greater number of specimens to be irradiated and facilitates specimen removal and maintenance of the apparatus.

Figure 4:
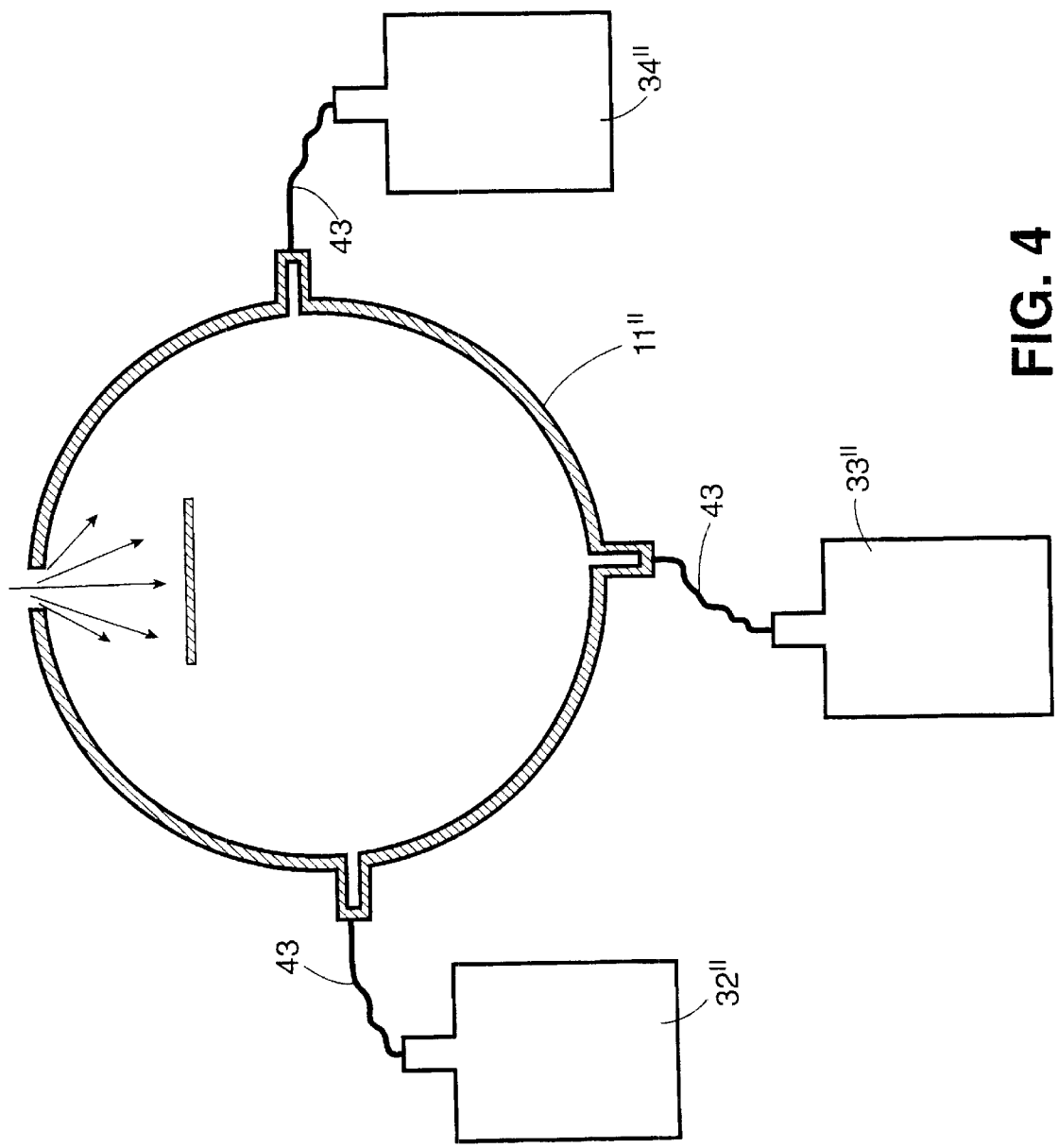
FIG. 4 is a cut-away plan view of another alternative embodiment of the integrating sphere of the apparatus of the invention.

For example, as shown in FIG. 4, the conduits 43 each may comprise a fiber optic connection 45, including one or more fiber optic cables, for communicating light from the sphere 11" to specimen holders 32", 33", 34". The conduit may alternatively comprise a "light pipe," or radiation guide (not shown). In another embodiment of the invention, as shown in FIG. 3, each conduit 43' comprises a cylindrical tube, preferably a right circular cylindrical tube. FIGS. 5 and 6 illustrate one embodiment of a cylindrical tube 43' in accordance with the invention, as shown assembled with a specimen holder 46. Couplings (not shown) such as screws or bolts or other optical mounts may be used to removably fasten the specimen holder 46 to the conduit 43' and/or the conduit 43' to an integrating sphere. The inner surface 47 of the tube preferably is mirror-like and may comprise, for example, polished aluminum. Preferably, the inner surface 47 is not diffusely reflective.

Figure 7:
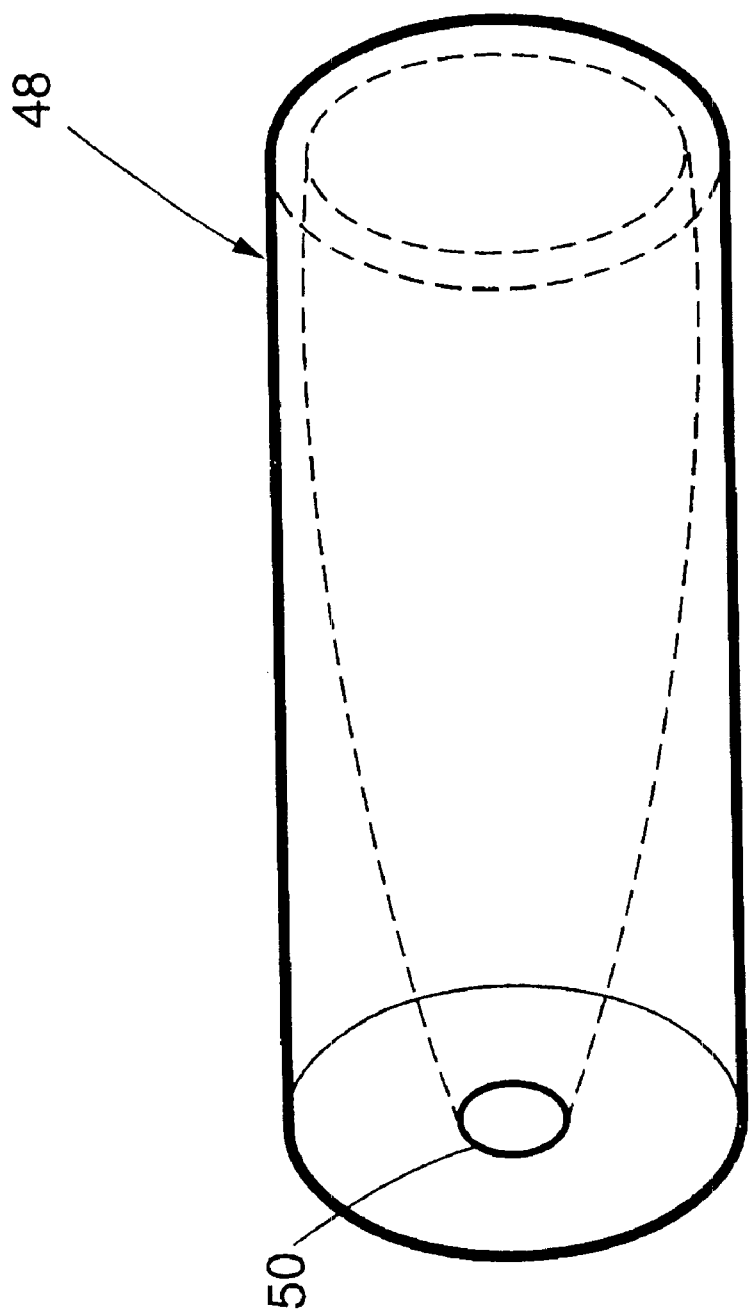
FIG. 7 is a perspective view of another embodiment of a conduit for an apparatus in accordance with the invention.
Figure 8:
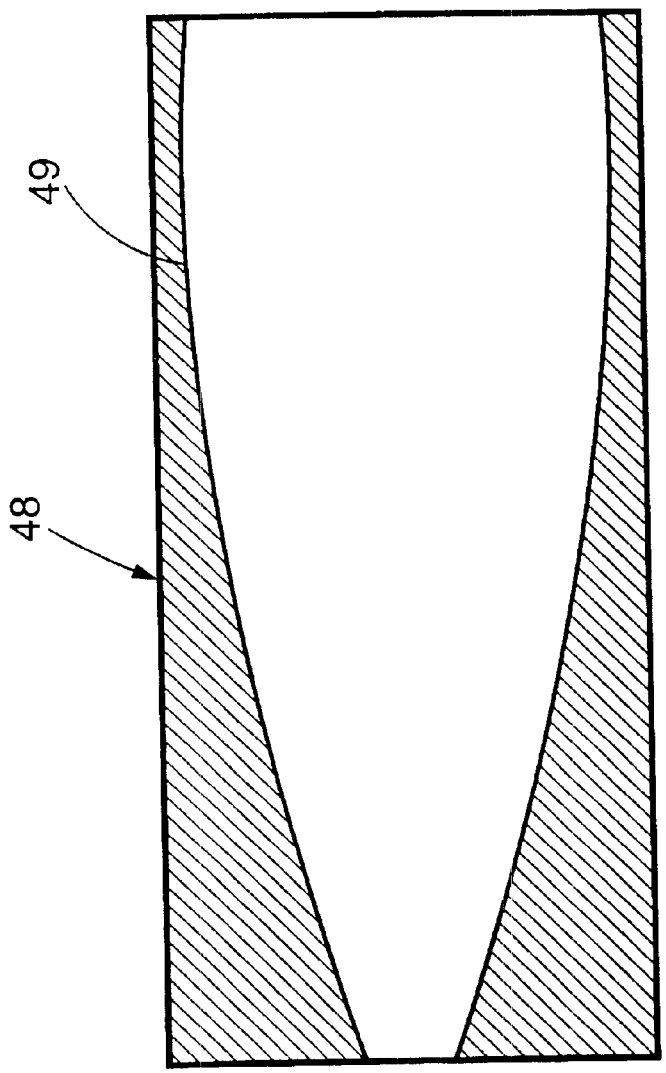
FIG. 8 is a cut-away side elevational view of the conduit shown in FIG. 7.

In a highly preferred embodiment of the invention, the conduit comprises a high collection, non-imaging optic device, such as compound parabolic cone concentrator 48, as shown in FIGS. 7 and 8. A compound parabolic cone concentrator, often referred to in the art as a Winston cone, is a non-imaging concentrator having an interior surface defining a surface of revolution of complex geometry. As shown in FIG. 8, the interior wall 49 of the compound parabolic cone concentrator 48 comprises a surface of revolution of an off-axis parabola. The surface geometry of such cones reflect and concentrate radiation while maintaining spatial uniformity of radiant energy flux over the cross-section of the cone. Physical principles of such cones are discussed in Welford et al., *The Optics of Nonimaging Concentrators: Light and Solar Energy* (1978) and Welford et al., *High Collection Nonimaging Optics* (1989). Such cones have heretofore been used in conjunction with light collection in optical systems. When used in accordance with the apparatus of the present invention, radiant energy flux is concentrated while retaining flux uniformity across a cross-section normal to the beam. The end 50 of the cone 48 having the smaller cross-section preferably is connected to the specimen holder and the other end of the cone preferably is connected to the integrating sphere.

The apparatus of the invention preferably is used in conjunction with a method for irradiating a specimen with a beam of radiation, preferably ultraviolet radiation. In accordance with a preferred embodiment of the invention, the method comprises the steps of providing an integrating sphere in radiative communication with a source of radiation, and placing one or more specimens (for example specimens S, $S_1$ shown in FIG. 2) in radiative communication with the integrating sphere. Preferably, the method is performed using the apparatus of the invention as hereinbefore described.

In a preferred embodiment of the invention, the method includes the step of measuring a change in one or more properties of the specimen. For example, when the property is one whose change may be observed on a molecular level, the step of measuring may comprise, for example, spectrographically analyzing the specimen. When the property is one whose change may be observed macroscopically, the change may be measured by observing a the change, such as, for example, by measuring the conductivity of the specimen, by weighing the specimen, by observing a color change in the specimen, or by evaluating the mechanical properties of the specimen. The length of time necessary to cause an observable change in the specimen will vary widely with the type of specimen and the radiation flux within the sphere. It is anticipated that the length of time may range from as short as a few seconds, to one hour, to twenty-four hours, to three days, to thirty days, to more than 100 days. When such apparatus is employed in conjunction with the method of the invention, a number of advantages are realized. For example, the apparatus allows great flexibility in the selection of a radiation source and the interchanging of specimens, and allows for one or more environmental conditions other than irradiance to be monitored and controlled. It is therefore seen that the foregoing general objects have been satisfied by the method and apparatus of the invention.

While particular embodiments of the invention have been shown, it will of course be understood that the invention is not limited thereto since modifications may be made by those skilled in the art, particularly in light of the foregoing teachings. It is, therefore, contemplated by the appended claims to cover any such modifications as incorporated in those features which constitute the essential features of these improvements within the true spirit and scope of the invention. All references cited herein are hereby incorporated by reference in their entireties.

What is claimed is:

1. A method for artificially weathering a specimen, comprising the steps of:
   providing an integrating sphere and a radiation source in radiative communication with the interior of said integrating sphere, the radiation flux within said integrating sphere being uniform;
   providing a specimen,
   placing said specimen in radiative communication with said integrating sphere; and
   irradiating said specimen for a length of time sufficient to cause a property of said specimen to measurably change and measuring said change.

2. A method according to claim 1, wherein said integrating sphere includes an exit aperture for emitting radiation having a width and a substantially uniform radiance over said width; wherein said specimen is external to but in radiative communication with said aperture.

3. A method according to claim 1, further comprising the steps of:
   providing a specimen holder disposed externally with respect to said integrating sphere, said integrating sphere radiatively communicating with said specimen holder through a conduit external to said integrating sphere; and
   placing a specimen in said holder prior to irradiating said specimen.

4. A method according to claim 1, wherein said irradiating is with a radiation beam having an area and a substantially uniform radiance over said area.

5. Method according to any of claim 1, wherein said radiation source is disposed externally with respect to said integrating sphere.

6. A method according to any of claim 1, wherein said radiation comprises ultraviolet light.

7. A method according to any of claim 1, wherein said length of time is at least 1 hour.

8. A method according to any of claim 1, the method including the steps of irradiating plural specimens each with a beam of radiation.

9. A method for irradiating plural specimens each with a beam of radiation, the method comprising the steps of:
   providing an integrating sphere having plural apertures including at least first and second aperture and providing a radiation source in radiative communication with the interior of said integrating sphere,
   communicating radiation from said integrating sphere through said apertures, said radiation comprising first and second radiation beams communicated respectively from said first and second apertures, said radiation beams having a substantially uniform radiance from beam to beam, each of said radiation beams having a width and a substantially uniform radiance over said width;
   providing at least two specimens;
   placing a first specimen in radiative communication with said integrating sphere through said first aperture;
   placing a second specimen in radiative communication with said integrating sphere through said second aperture;
   irradiating said first specimen with at least a portion of said radiation communicated through said first aperture;
   irradiating said second specimen with at least a portion of said radiation communicated through said second aperture; and,
   measuring a change in at least one property of the specimens;
   wherein said first specimen is disposed in a first specimen holder, said first specimen holder being disposed externally with respect to said integrating sphere and comprising a chamber substantially enclosing said first specimen, said integrating sphere radiatively communicating with said first specimen holder through a conduit external to said integrating sphere; and
   wherein said second specimen is disposed in a second specimen holder, said second specimen holder being disposed externally with respect to said integrating sphere and comprising a chamber substantially enclosing said second specimen, said integrating sphere radiatively communicating with said second specimen holder through a conduit external to said integrating sphere.

10. A method according to claim 9, wherein said conduit comprises a cylindrical channel.

11. A method according to claim 9, wherein said conduit comprises a compound parabolic cone concentrator.

12. A method for irradiating plural specimens each with a beam of radiation, the method comprising the steps of:

providing an integrating sphere having plural apertures including at least first and second aperture and providing a radiation source in radiative communication with the interior of said integrating sphere, communicating radiation from said integrating sphere through said apertures, said radiation comprising first and second radiation beams communicated respectively from said first and second apertures, said radiation beams having a substantially uniform radiance from beam to beam, each of said radiation beams having a width and a substantially uniform radiance over said width;

providing at least two specimens;

placing a first specimen in radiative communication with said integrating sphere through said first aperture;

placing a second specimen in radiative communication with said integrating sphere through said second aperture; and irradiating said first specimen with at least a portion of said radiation communicated through said first aperture;

irradiating said second specimen with at least a portion of said radiation communicated through said second aperture; and, measuring a change in at least one property of the specimens;

wherein said first specimen is disposed in a first specimen holder, said first specimen holder being disposed externally with respect to said integrating sphere and comprising a chamber substantially enclosing said first specimen, said integrating sphere radiatively communicating with said first specimen holder through a conduit external to said integrating sphere; and wherein said second specimen is disposed in a second specimen holder, said second specimen holder being disposed externally with respect to said integrating sphere and comprising a chamber substantially enclosing said second specimen, said integrating sphere radiatively communicating with said second specimen holder through a conduit external to said integrating sphere, the method further comprising the steps of providing a first environmental condition in said first specimen holder and providing a second environmental condition in said second specimen holder, said second environmental condition differing from said first environmental condition.

13. A method according to claim 12, wherein the humidity in said first specimen holder differs from the humidity in said second specimen holder.

14. A method according to claim 12, wherein the temperature in said first specimen holder differs from the temperature in said second specimen holder.

15. A method according to claim 12, wherein a first mechanical load is applied to said first specimen and a second load mechanical load selected from the group consisting of no mechanical load, a mechanical load greater than said first mechanical load, and a mechanical load less than said first mechanical load is applied to said second specimen.

16. A method for irradiating plural specimens each with a beam of radiation, the method comprising the steps of:

providing an integrating sphere having plural apertures including at least first and second aperture and providing a radiation source in radiative communication with the interior of said integrating sphere, communicating radiation from said intergrating sphere through said apertures said radiation comprising first and second radiation beams communicated respectively from said first and second apertures, said radiation beams having a substantially uniform radiance from beam to beam, each of said radiation beams having a width and a substantially uniform radiance over said width;

providing at least two specimens;

placing a first specimen in radiative communication with said integrating sphere through said first aperture;

placing a second specimen in radiative communication with said integrating sphere through said second aperture;

irradiating said first specimen with at least a portion of said radiation communicated through said first aperture;

irradiating said second specimen with at least a portion of said radiation communicated through said second aperture; and, measuring a change in at least one property of the specimens;

wherein said first specimen is disposed in a first specimen holder, said first specimen holder being disposed externally with respect to said integrating sphere and comprising a chamber substantially enclosing said first specimen, said integrating sphere radiatively communicating with said first specimen holder through a conduit external to said integrating sphere;

wherein said second specimen is disposed in a second specimen holder, said second specimen holder being disposed externally with respect to said integrating sphere and comprising a chamber substantially enclosing said second specimen, said integrating sphere radiatively communicating with said second specimen holder through a conduit external to said intergrating sphere; and wherein at least one of the said conduits comprises a fiber optic connection.

17. Apparatus comprising:

an integrating sphere having first and second apertures;

a radiation source in radiative communication with the interior of said integrating sphere, whereby beams of radiation each having a width and a substantially uniform radiance over said width are communicated from said integrating sphere through said first and second apertures; and first and second specimen holders, said first specimen holder disposed externally with respect to said integrating sphere and said integrating sphere radiatively communicating with said first specimen holder through said first aperture, said second specimen holder disposed externally with respect to said integrating sphere and said integrating sphere radiatively communicating with said second specimen holder through said second aperture;

wherein each of said first and second apertures comprises a substantially enclosed chamber, the apparatus further including means for varying an environmental condition in at least one of said first and second specimen holders.

18. Apparatus according to either of claim 17, including:

a first conduit connected to said integrating sphere at said first aperture and a second conduit connected to said integrating sphere at said second aperture, said integrating sphere radiatively communicating with said first specimen holder through said first conduit and said integrating sphere radiatively communicating with said second specimen holder through said second conduit.

19. Apparatus according to claim 18, wherein each of said first and second conduits is a cylindrical channel.

20. Apparatus according to claim 18, wherein each of said first and second conduits is a fiber optic connection.

21. Apparatus according to claim 18, wherein each of said first and second conduits is a high collection non-imaging optic device.

22. Apparatus according to claim 18, including first, second and third conduits connected to said integrating sphere at said first, second, and third apertures respectively, said integrating sphere radiatively communicating with said specimen holders through respective conduits.

23. Apparatus according to claim 17, wherein said means varying comprises means for controlling the temperature in at least one of said first and second specimen holder.

24. Apparatus according to claim 17 wherein said means for varying comprises means or controlling the ambient humidity in at least one of said first and second specimen holders.

25. Apparatus according to claim 17, wherein said means or varying comprises means for applying a mechanical load to a specimen in at least one of said first and second specimen holders.

26. Apparatus comprising:

an integrating sphere having first and second apertures;

a radiation source in radiative communication with the interior of said integrating sphere, whereby beams of radiation each having a width and a substantially uniform radiance over said width are communicated from said integrating sphere through said first and second apertures; and first and second specimen holders, said first specimen holder disposed externally with respect to said integrating sphere and said integrating sphere radiatively communicating with said first specimen holder through said first aperture, said second specimen holder disposed externally with respect to said integrating sphere and said integrating sphere radiatively communicating with said second specimen holder through said second aperture;

wherein said integrating sphere includes a third aperture, the apparatus further comprising a third specimen holder dispersed externally with respect to said integrating sphere and said integrating sphere radiatively communicating with said third specimen holder through said third aperture.

\* \* \* \* \*

UNITED STATES PATENT AND TRADEMARK OFFICE
CERTIFICATE OF CORRECTION

PATENT NO. : 6,626,052 B1
DATED : September 30, 2003
INVENTOR(S) : Jonathan Martin et al.

It is certified that error appears in the above-identified patent and that said Letters Patent is hereby corrected as shown below:

Column 13,
Line 19, reads "varying" should read -- for varying --
Line 20, reads "holder" should read -- holders --
Lines 22 and 26, reads "or" should read -- for --

Signed and Sealed this

Eleventh Day of January, 2005

JON W. DUDAS
*Director of the United States Patent and Trademark Office*